(12) United States Patent
Clayton et al.

(10) Patent No.: US 10,280,318 B2
(45) Date of Patent: May 7, 2019

(54) MONOMERS AND OLIGOMERS WITH APPLICATION IN ENERGY CURING CHEMISTRY

(71) Applicant: Electronics for Imaging, Inc., Fremont, CA (US)

(72) Inventors: Terrill Scott Clayton, Colorado Springs, CO (US); Bruce Klemann, Concord, NH (US); Lianhui Cong, Concord, NH (US); Fengying Shi, Westford, MA (US)

(73) Assignee: ELECTRONICS FOR IMAGING, INC., Fremont, CA (US)

( * ) Notice: Subject to any disclaimer, the term of this patent is extended or adjusted under 35 U.S.C. 154(b) by 74 days.

(21) Appl. No.: 15/135,341

(22) Filed: Apr. 21, 2016

(65) Prior Publication Data

US 2016/0312051 A1    Oct. 27, 2016

Related U.S. Application Data

(60) Provisional application No. 62/151,940, filed on Apr. 23, 2015.

(51) Int. Cl.
*C09D 11/101* (2014.01)
*C07D 307/14* (2006.01)
*C09D 11/10* (2014.01)

(52) U.S. Cl.
CPC .......... *C09D 11/101* (2013.01); *C07D 307/14* (2013.01); *C09D 11/10* (2013.01)

(58) Field of Classification Search
CPC ...... C07D 307/14; C09D 11/101; C09D 11/10
See application file for complete search history.

(56) References Cited

U.S. PATENT DOCUMENTS

| | | | |
|---|---|---|---|
| 4,303,924 A | 12/1981 | Young et al. | |
| 4,351,881 A | 9/1982 | Kamada et al. | |
| 4,933,260 A | 6/1990 | Katsumata et al. | |
| 5,047,443 A | 9/1991 | Rehmer | |
| 6,255,444 B1* | 7/2001 | Yuasa | C07C 69/76 525/309 |
| 7,365,105 B2 | 4/2008 | Kiefer-Liptak et al. | |
| 7,897,718 B2 | 3/2011 | Chang et al. | |
| 8,133,539 B2 | 3/2012 | Oberski et al. | |
| 8,475,996 B2 | 7/2013 | Aoai et al. | |
| 8,889,232 B2 | 11/2014 | Cong | |
| 2006/0222831 A1 | 10/2006 | Sloan et al. | |

FOREIGN PATENT DOCUMENTS

EP    0655465 A1    5/1995
WO    2015131029 A1    9/2015

OTHER PUBLICATIONS

Supplementary Partial European Search Report dated Oct. 5, 2018 for European Patent Application No. 16783996.8 of Electronics for Imaging, Inc., 10 pages.

* cited by examiner

*Primary Examiner* — Jessica M Roswell
(74) *Attorney, Agent, or Firm* — Perkins Coie LLP

(57) ABSTRACT

Embodiments of the invention have application in the field of inkjet inks. Additionally, the novel energy cure monomers and oligomers disclosed herein also have application more broadly in the field of energy cure inks and coatings.

7 Claims, 4 Drawing Sheets

THFA                                    COMPOUND 1

THFA                    COMPOUND 1

Example of polyether

Example of polyethylene glycol $n = 1\text{-}10$

MONOMERS AND OLIGOMERS WITH APPLICATION IN ENERGY CURING CHEMISTRY

CROSS REFERENCE TO RELATED APPLICATIONS

This application claims priority to U.S. provisional patent application Ser. No. 62/151,940, filed Apr. 23, 2015, which is incorporated herein in its entirety by this reference thereto.

FIELD

The invention relates to energy curable inks. More particularly, the invention relates to novel monomers and oligomers with application in energy curing chemistry.

BACKGROUND

Monomers for use in energy curable inks and coatings are well known. Sartomer, IGM, Allnex and others have been supplying a wide range of monomers for formulation. Many commonly used monomers are off patent and have been commoditized. There is very little innovation underway by the major suppliers of monomers and oligomers. Commonly used monofunctional monomers for UV curing include methoxy polyethylene glycol (550) monoacrylate, aromatic acrylate monomer, aromatic alcohols, alkoxylated lauryl acrylates, cycloaliphatic acrylate monomer, 2(2-ethoxyethoxy) ethyl acrylate, stearyl acrylate, acrylate ester, tetrahydrofurfuryl acrylate, lauryl acrylate, 2-phenoxyethyl acrylate, isodecyl acrylate, acrylic monomer, isooctyl acrylate, octyldecyl acrylate, tridecyl acrylate, caprolactone acrylate, ethoxylated 4-nonyl phenol acrylate, isobornyl acrylate, cyclic trimethylolpropane formal acrylate, methoxy polyethylene glycol (350) monoacrylate, 2-Propenoic acid, octadecyl ester, alkoxylated tetrahydrofurfuryl acrylate, alkoxylated phenol acrylate, 1,4-Butanediol Monoacrylate, benzyl acrylate, aliphatic urethane. Acrylate, 4-t-butylcyclohexyl acrylate, dioxolane Acrylate, 3, 3, 5-trimethyl cyclohexyl acrylate, benzyl acrylate, nonyl phenol (4EO) acrylate, phenol (2,5 EO) acrylate, 2-(butylaminolcarbnyl)oxyethyl acrylate, and octyldecyl acrylate.

A nonlimiting list of difunctional monomers include cyclohexane dimethanol diacrylate, alkoxylated hexanediol diacrylate, alkoxylated hexanediol diacrylate, alkoxylated hexanediol diacrylate, 1,10-decanediol diacrylate, acrylate ester, alkoxylated neopentyl glycol diacrylate, 1,3-butylene glycol diacrylate, 2-propenoic acid, 1,4-butanediyl ester, diethylene glycol diacrylate, 1,6 hexanediol diacrylate, neopentyl glycol diacrylate, polyethylene glycol (200) diacrylate, tetraethylene glycol diacrylate, triethylene glycol diacrylate, tripropylene glycol diacrylate, methypentanediol diacrylate, polyethylene glycol (400) diacrylate, ethoxylated (3) bisphenol a diacrylate, dipropylene glycol diacrylate, alkoxylated hexanediol diacrylate, ethoxylated (4) bisphenol a diacrylate, ethoxylated (10) bisphenol a diacrylate, polyethylene glycol (600) diacrylate, tricyclodecane dimethanol diacrylate, propoxylated (2) neopentyl glycol diacrylate, ethoxylated (30) bisphenol a diacrylate, alkoxylated aliphatic diacrylate, 1,9-nonanediol diacrylate, hexanediol (2 EO) diacrylate, and hexanediol (2 PO) diacrylate.

Due to recent changes in international regulatory rules, most of the key monomers used in energy cure chemistry can no longer be used in ink and coating formulation, and those which can be used do not perform adequately, i.e. they do not perform well with regard to surface cure, adhesion, flexibility, etc. Further, with the advent of environmentally friendly UV LED type curing lamp technologies, traditional UV monomers and oligomers cannot cure efficiently, resulting in incompletely cured inks and coatings. Innovation around formulations and raw materials for UV curable inks and coatings is desperately needed.

SUMMARY

Embodiments of the invention have application in the field of inkjet inks. Additionally, the novel energy cure monomers and oligomers disclosed herein also have application more broadly in the field of energy cure inks and coatings.

DRAWINGS

DESCRIPTION

Embodiments of the invention have application in the field of inkjet inks. Additionally, the novel energy cure monomers and oligomers disclosed herein also have application more broadly in the field of energy cure inks and coatings.

Ultraviolet radiation curable coatings are built on acrylate chemistry which contains an ester functionality. Esterases in biological organisms can hydrolyze or metabolize the acrylate esters to alcohol derivatives. In the case of THFA, esterases convert it to a tetrahydrofurfuryl alcohol. Many of these types of monomers have been determined to carcinogenic or are otherwise classified as toxic. Currently available monomers with acceptable curing properties that are within regulatory compliance do not exist for UV LED curing.

One aspect of the herein disclosed invention is the design and synthesis of novel monomers and oligomers which maintain the desirable properties of monomers, while constructing them in a way in which do have the toxic effect in living organisms. As an example, tetrahydrofurfyl acrylate is energy curable monomer with desirable physical properties in UV curable inkjet ink. However, it has been classified as a CMR (carcinogenic, mutagenic and reprotoxic substances). The reason for this classification results from the fact that the acrylate functional group can be metabolized to an alcohol which has been determined to be toxic.

Bioisoteres are well known in the field of synthetic chemistry and have been used to modify the functionality of pharmaceuticals and secondary metabolites. Amides, imidazoles, and ethers have been used as bioisosteres of esters successfully in medicinal chemistry to improve efficacy of drugs, as disclosed by Clayton et al. in U.S. Pat. No.

7,595,395 B2 and US 20100130479 A1. Bioisosteres have been used to improve efficacy and bioavailability of drugs by significantly reducing or eliminating esterase metabolism in the body.

Figure 1:
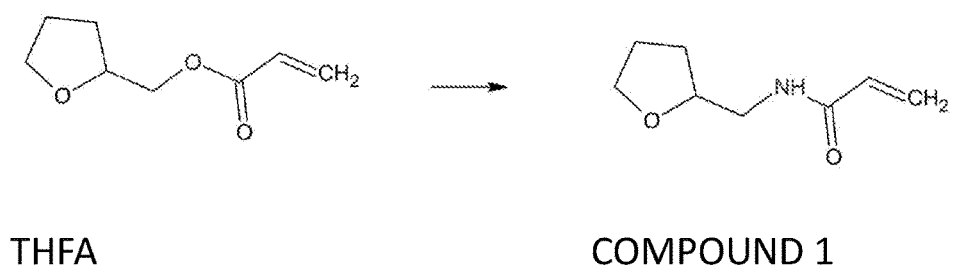
FIG. 1 shows the modification of THFA to an amide acrylate according to the invention.

Modifying tetrahyrofurfuryl acrylate (THFA) (CAS # 2399-48-6), a key monomer used in UV LED ink formulation for cure and adhesion, to an amide acrylate (ester acrylate bioisostere) analog maintains all of the key performance properties for inkjet ink, while eliminating the toxic effects in biological organisms by esterase metabolism to the alcohol derivative. See FIG. 1, which shows the modification of THFA to an amide acrylate according to the invention.

Figure 2:
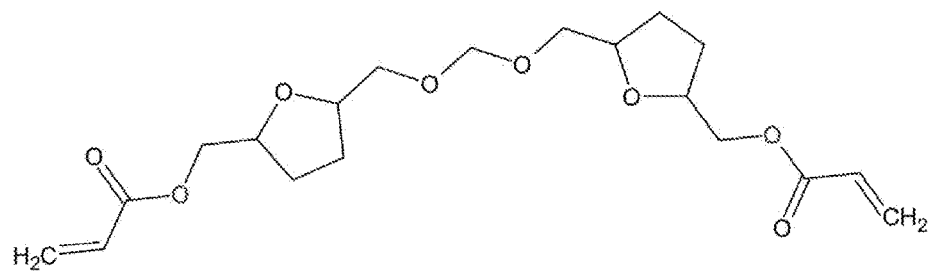
FIG. 2 shows a dimer of THFA tethered by an ether linkage according to the invention.

Low viscosity oligomers, based on traditional monomers tethered with multiple ether groups, may provide abstractable hydrogens to a peroxy radical to reinitiate polymerization and also overcome oxygen inhibition. By way of a nonlimiting example, consider a dimer of THFA tethered by an ether linkage. This difunctional oligomer offers the benefits of THFA, low viscosity, and the hydrogen donors to overcomer oxygen inhibition. FIG. 2 shows a dimer of THFA tethered by an ether linkage according to the invention.

In addition to dimers, trimers, tetramers, and higher order oligomers have utility in the invention.

Figure 3:
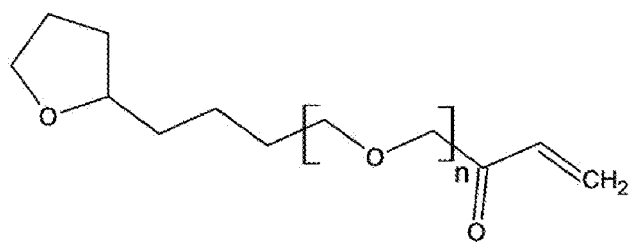
FIG. 3 shows the introduction of ether groups and ethylene glycol according to the invention.
Figure 3:
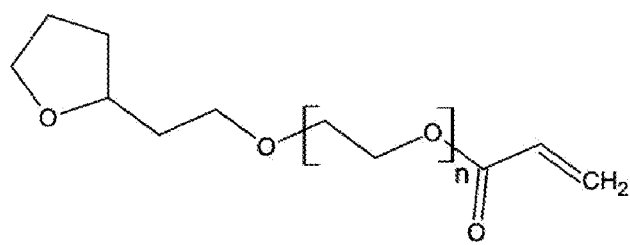
Figure 3:
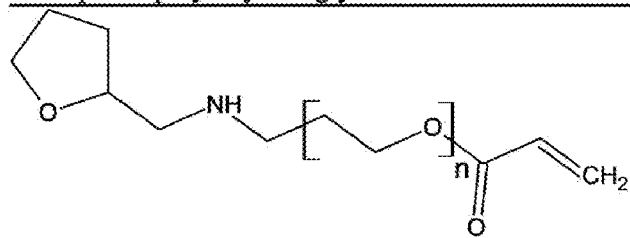

Additionally, to adjust the flexibility of these new difunctional oligomers, ether groups and ethylene glycol can be introduced with n=1-1000. FIG. 3 shows the introduction of ether groups and ethylene glycol according to the invention.

Figure 4:
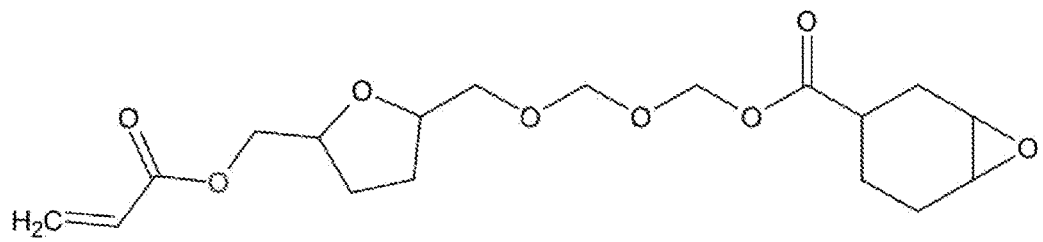
FIG. 4 shows the use of oligomers with a multifunctional approach according to the invention.

Another strategy is to combine the benefits of THFA with the cure properties of epoxide systems which cure via a cationic mechanism. Using oligomers with this multifunctional approach results in solid surface cure and minimal post cure shrinkage. An additional benefit of the epoxide is that it is not inhibited by oxygen. FIG. 4 shows the use of oligomers with a multifunctional approach according to the invention.

The difunctional oligomer also contains ether linkages providing abstractable hydrogens to reinitiate polymerization terminated by peroxy radicals formed by oxygen. Such an ink system for inkjet ink formulation can be further viscosity reduced using an oxetane monomer, such as trimethylolpropane oxetane or 3-ethyl-3-hydroxymethyl-oxetane. The epoxide can also be replaced with a vinyloxy or vinyloxy ethoxy group if cationic curing is desired.

Figure 5:
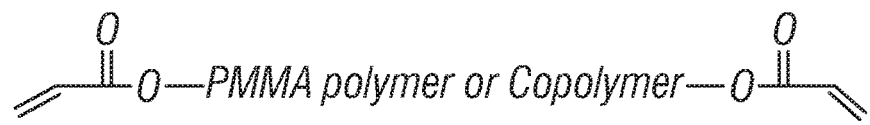
FIG. 5 shows combining the novel monomers with a novel oligomer acrylate single or dual capped PMMA according to the invention.

Further, combining the novel monomers with a novel oligomer acrylate single or dual capped PMMA (polymethylmethacrylate) resin further enhances adhesion to substrates, including coroplast, polyethylene, polypropylene, and acrylics. FIG. 5 shows combining the novel monomers with a novel oligomer acrylate single or dual capped PMMA according to the invention.

Another useful polymer with good adhesion to substrates includes a tetrahydrofurfuryl acrylate single or double capped PMMA polymer.

Figure 6:
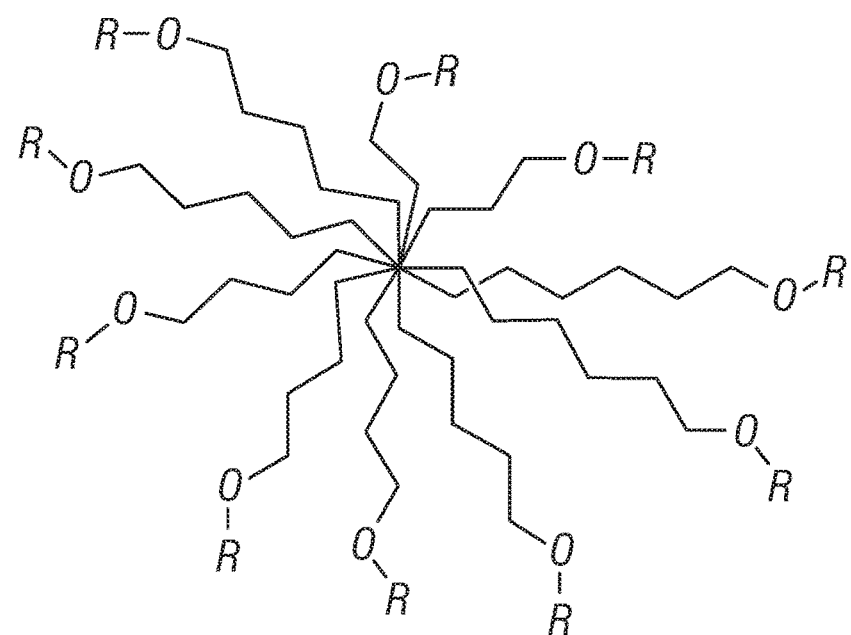
FIG. 6 shows the use of hyperbranched oligomers according to the invention.
Figure 6:
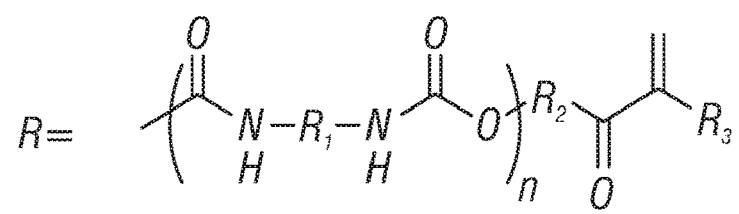

Another useful polymer which can enhance surface cure without resulting in a brittle film and undesireable shrinkage is a tetrahydrofurfuryl based hyperbranched acrylate, urethane acrylate or ethoxylated acrylate or vinyl ether. The polarity and reactivity can be tuned by the selection of dendritic branches, as well as the choice of monomer (R). The curing mechanism can be solely UV radiation free radical, cationic, anionic, or a combination of more than one. These hyperbranched oligomers enhance the cure properties, such as adhesion and toughness, while maintaining a lower viscosity as compared to traditional urethane acrylates, and do not reduce flexibility of the cured film. FIG. 6 shows the use of hyperbranched oligomers according to the invention.

Figure 7:
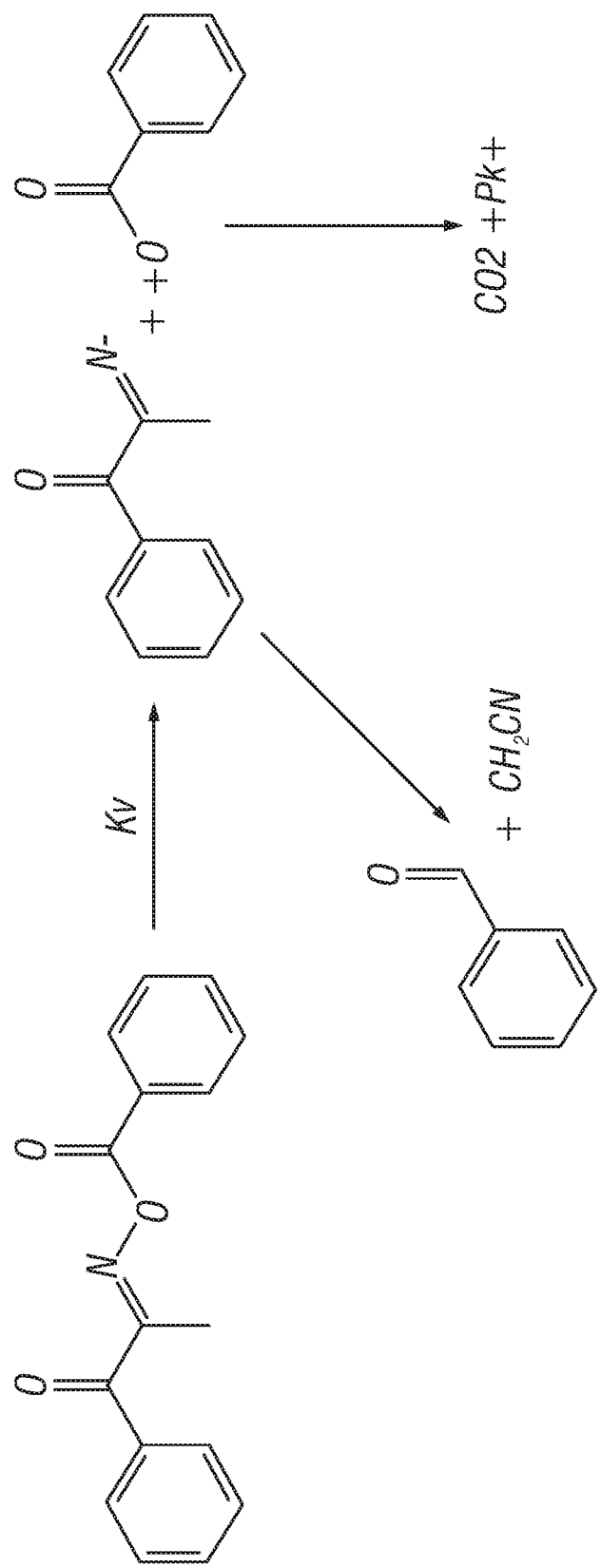
FIG. 7 shows acyloxime esters generating carbon dioxide after exposure to ultraviolet radiation and releasing a radical initiator according to the invention.

Acyloxime esters can generate carbon dioxide after exposure to ultraviolet radiation and release a radical initiator. See FIG. 7. This results in an inerted ink to improve surface curing in UV radiation curable systems. Enhancement of adhesion and speed of cure can be achieved by attaching the acrylate functionality, such as THFA, PEA type monomers to aromatic ring or other locations to get the combination of initiator and monomer. This is another approach to using the benefits of idealized monomers without the odor, safety, and regulatory concerns associated with them, i.e. THFA, VCAP, IBOA.

The monomers and oligomers of the invention allow for the formulation of inkjet ink which is safer to work with while retaining key performance properties.

Further, the novel monomers and oligomers have excellent reactivity for use in UV LED curing systems and reduce or eliminate the need for nitrogen or other inert blanketing.

There is significant value to the invention because inkjet ink production is a billion dollar industry. Inks with more regulatory friendly labeling offer a significant commercial value to producers. These inks allow for printers to be built without costly onboard nitrogen generators for curing. Inks which are more regulatory friendly, have enhanced cure properties, do not require nitrogen blanketing, and provide a significant advantage over state of the art products.

EXAMPLES

Example 1

Cyan Ink Composition

Table 1 shows the components for a cyan ink composition.

TABLE 1

| Trade Name | Chemical | Cyan Ink weight % |
|---|---|---|
| SR531 | CTFA (cyclic trimethylolpropane formal acrylate, mono-functional monomer) | 24.65 |
| Compound 1 | N-[(oxolan-2-yl)methyl]prop-2-enamide | 25.5 |
| SR506 | IBOA (isobornyl acrylate, mono-functional monomer) | 12.0 |
| CN991 | Urethane Acrylate Oligomer | 10.0 |
| V-Cap | N-Vinyl Caprolactam (mono-functional monomer) | 9.50 |
| SR9003 | PONPGDA (difunctional monomer) | 3.0 |
| BYK-361N | Polyacrylate Additive | 0.50 |
| BYK-377 | Polyester Modified Polydimethyl Siloxane (Surfactant) | 0.050 |
| Irgastab UV22 | In-can stabilizer | 1.0 |
| DOVERPHOS ® 12 | Phosphite (Anti-Oxidant) | 2.0 |

TABLE 1-continued

| Trade Name | Chemical | Cyan Ink weight % |
|---|---|---|
| Genocure TPO | Acylphosphine Oxide, MAPO (photoinitiator) | 10.0 |
| Cyan pigments | Pigments | 1.8 |
| | | 100.0 |

Example 2

Cyan Ink Composition using Compound 1

Table 2 shows the components for a more regulatory cyan ink composition.

TABLE 2

| Trade Name | Chemical | Cyan Ink weight % |
|---|---|---|
| SR531 | CTFA (cyclic trimethylolpropane formal acrylate, mono-functional monomer) | 24.65 |
| Compound 1 | N-[(oxolan-2-yl)methyl]prop-2-enamide | 25.5 |
| SR506 | IBOA (isobornyl acrylate, mono-functional monomer) | 12.0 |
| CN991 | Urethane Acrylate Oligomer | 10.0 |
| V-Cap | N-Vinyl Caprolactam (mono-functional monomer) | 9.50 |
| SR9003 | PONPGDA (difunctional monomer) | 3.0 |
| BYK-361N | Polyacrylate Additive | 0.50 |
| BYK-377 | Polyester Modified Polydimethyl Siloxane (Surfactant) | 0.050 |
| Irgastab UV22 | In-can stabilizer | 1.0 |
| DOVERPHOS ® 12 | Phosphite (Anti-Oxidant) | 2.0 |
| Genocure TPO | Acylphosphine Oxide, MAPO (photoinitiator) | 10.0 |
| Cyan pigments | Pigments | 1.8 |
| | | 100.0 |

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. An ultraviolet radiation curable coating comprising: a dimer of tetrahydrofurfuryl acrylate tethered by an ether linkage:

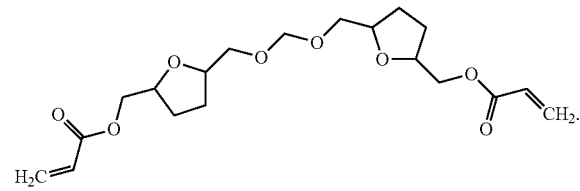 [SMILES: C=CC(=O)OCC1CCC(COCOCC2CCC(COC(=O)C=C)O2)O1]

2. An ultraviolet radiation curable coating comprising a difunctional oligomer:

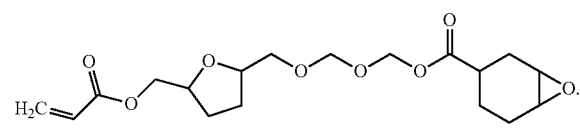 [SMILES: C=CC(=O)OCC1CCC(COCOCOC(=O)C2CCC3OC3C2)O1]

3. The coating of claim 2, further comprising an oxetane monomer of
   trimethylolpropane oxetane or 3-ethyl-3-hydroxymethyl-oxetane.

4. An ultraviolet radiation curable coating, comprising N-[(oxolan-2-yl) methyl]prop-2-enamide and an oligomer acrylate single or dual capped PMMA (polymethylmethacrylate) resin.

5. An ultraviolet radiation curable coating, comprising N-[(oxolan-2-yl) methyl]prop-2-enamide and a tetrahydrofurfuryl acrylate single or double capped polymethylmethacrylate polymer.

6. An ultraviolet radiation curable coating, comprising N-[(oxolan-2-yl)methyl]prop-2-enamide and a hyper-branched oligomer of a tetrahydrofurfuryl based hyperbranched acrylate.

7. An ultraviolet radiation curable coating, comprising:

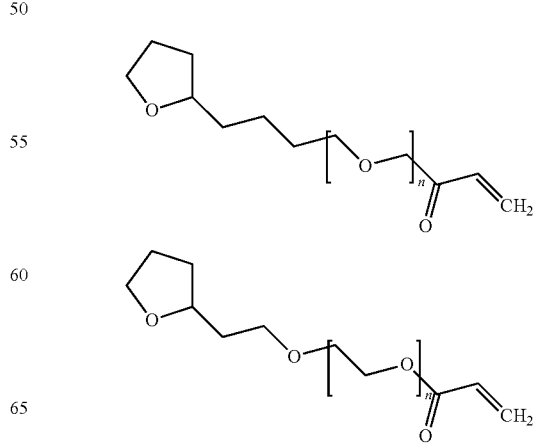

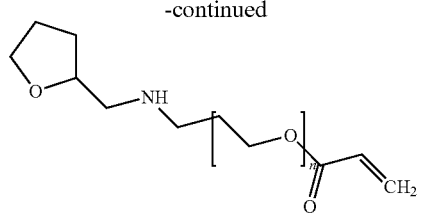
wherein n=1-1000.
* * * * *